United States Patent [19]

Tiitola et al.

[11] Patent Number: 4,917,105

[45] Date of Patent: Apr. 17, 1990

[54] FOOT TESTING METHOD

[75] Inventors: Antti-Jussi Tiitola, Kaivanto; Martti Kvist, Kuusisto, both of Finland

[73] Assignee: Karhu-Titan, Vantaa, Finland

[21] Appl. No.: 199,472

[22] Filed: May 27, 1988

[30] Foreign Application Priority Data

Dec. 24, 1987 [CA] Canada .................................. 555405

[51] Int. Cl.$^4$ ................................................ A61B 5/10
[52] U.S. Cl. .............................. 128/779; 128/80 DB; 33/515
[58] Field of Search ............. 128/774, 779, 782, 80 D, 128/80 DB, 581, 585, 586, 595, 614, 619, 898; 33/511, 512, 515, 3 A, 3 B, 3 C

[56] References Cited

U.S. PATENT DOCUMENTS

| | | | |
|---|---|---|---|
| 2,175,116 | 10/1939 | Hack et al. | 128/21 |
| 3,358,373 | 12/1967 | Martin | 128/779 |
| 4,062,355 | 12/1977 | Kaye | 128/779 |

Primary Examiner—Max Hindenburg
Assistant Examiner—Randy Shay
Attorney, Agent, or Firm—Fay, Sharpe, Beall, Fagan, Minnich & McKee

[57] ABSTRACT

This invention relates to a foot testing method to analyze the functional biomechanic type of the foot of a person such as an athlete to determine the appropriate insole to be fitted in the person's shoe as well as to a measuring device and insole used to implement this method. This method comprises the following steps: (1) placing the foot in a neutral (unloaded) position; (2) identifying the center line of the heel bone; (3) identifying the center line of the tendo Achillis; (4) placing the person tested in a standing position and preferably identifying the type of arch; (5) measuring the angle between the heel bone center line and the tendo Achillis center line preferably with his/her knees bent at approximately 45°.

31 Claims, 7 Drawing Sheets

| | A | | B | | | C | | |
|---|---|---|---|---|---|---|---|---|
| | | | LEFT | | | RIGHT | | |
| 1 | (figure: 50, 20, 15cm, 40, 10cm, 10) | | | | | | | |
| 2 | (figure: 110, 80, 90, 110) | | O >8 mm | N 8-2 mm | U 2mm > | O >8 mm | N 8-2 mm | U 2mm > |
| | | | 5 | 5 | 5 | 5 | 5 | 5 |
| 3 | (figure: A B C) | | A | B | C | A | B | C |
| | | | 2 | 2 | 2 | 2 | 2 | 2 |
| 4 | (figure: 235) | | > 8° | 8-5 mm | 5° > | >8° | 8-5 mm | 5° > |
| | | | 10 | 10 | 10 | 10 | 10 | 10 |
| 5 | (figure: 240, 250) | | >8 mm | 8-2 mm | 2mm > | >8 mm | 8-2 mm | 2mm > |
| | | | 8 | 8 | 8 | 8 | 8 | 8 |
| 6 | (figure: 260) | | | | | | | |
| | | | 5 | 5 | 5 | 5 | 5 | 5 |

FIG.1

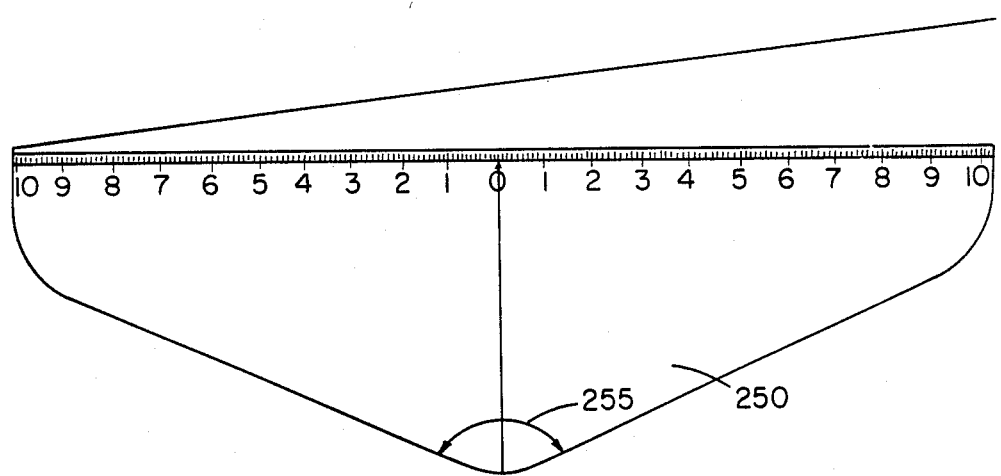
FIG. 5
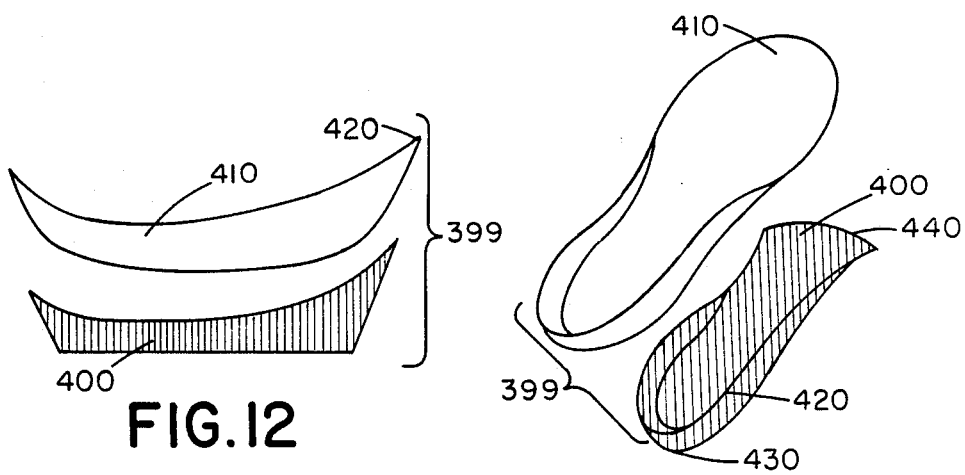
FIG. 12
FIG. 11

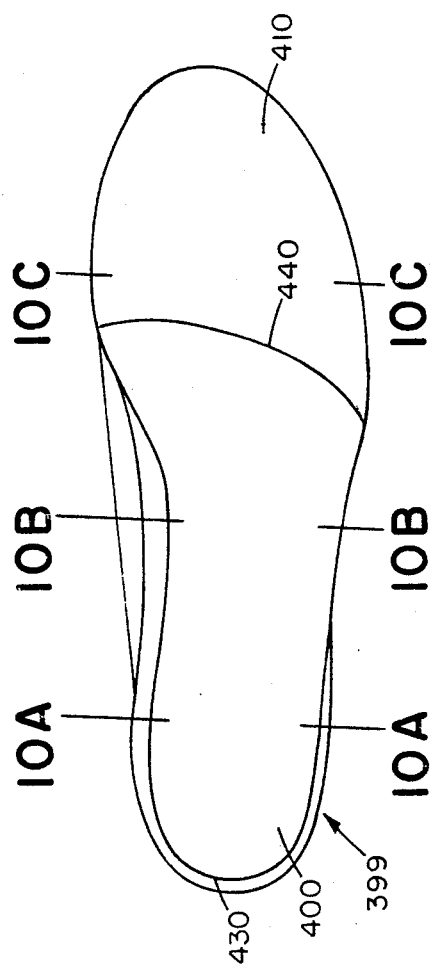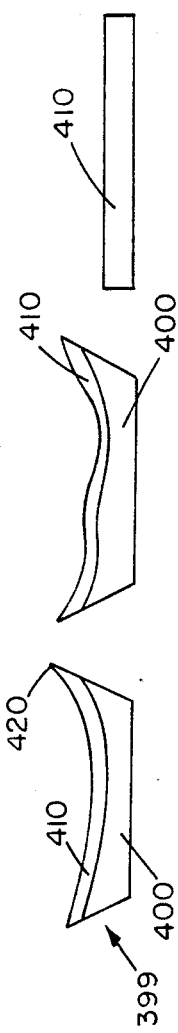
FIG. 10
FIG.10A
FIG.10B
FIG.10C

FOOT TESTING METHOD

FIELD OF THE INVENTION

This invention relates to a foot testing method to analyse the functional biomechanic type of the feet of a person such as an athlete as well as to a measuring device and insole used to implement the method.

DESCRIPTION OF PRIOR ART

The foot is a very complex mechanical structure. It has to be flexible to accommodate variations in the external environment while it is being used namely to balance and support the posture of the body.

The foot must also provide the friction with the ground and expresses the horizontal load of acceleration, deceleration or turns of the body.

However, the foot has been grossly neglected by most individuals as well as by professionals for different reasons. For example, some people suffer of foot disorders, but they think that their problems are not serious enough to require an examination or an advice and prefer living with them without knowing that their foot condition may deteriorate.

Furthermore, unlike the hand, which is designed essentially for grasping, the foot is fundamentally a weight-bearing organ, and we are accustomed to regard the hand as the great agent by which all the creative power is obtained and we are apt to forget how much we are indebted to the foot.

When the foot is not formed or supported adequately to bear the dynamic forces imposed by walking or running, it tends to adapt itself by creating deformations to same.

The most common types of abnormalities in the shape of the foot may be described as follows:

Calcaneus is the term used to describe a fixed dorsiflexed deformity of the foot in which the heel bears the entire weight of the body. Dorsiflexion is the position wherein the foot is flexed upwardly toward the shin or lower leg.

Pes planus is Latin for flat foot.

Pes cavus means a foot with a fixed high arch.

Valgus and varus which describe angular deformities of the limbs.

Pronation may be described as a three plane motion involving, dorsiflexion, eversion and abduction at the subtalar joint. Pronation is a natural part of body's own shock absorbing system and it enables the foot to adapt itself to the ground. However, people have feet with different tendencies to pronation. Some feet are stiff, they do not pronate enough to create natural shock absorbtion, which causes risk for overuse injuries especially in tendo Achillis, heel or knee joint. Statistically, 10-15% of people have feet with these characteristics. About 40% people have feet with a normal tendency for pronation and about 45% have a tendency to excessive pronation. Excessive pronation causes many problems for people who run or walk significantly or even stand in their daily work. The invention will provide a method to evaluate the foot tendency to pronation and also evaluate other abnormalities like high arch, flat foot, varus or valgus deformity of the forefoot and rearfoot.

Since shoes are generally manufactured on a production basis, the supporting surface of the interior of the shoe may or may not optimally locate the plantar surface of a particular foot. Therefore, as above mentioned, the foot is often not properly supported.

The most common technic used to correct said foot disorders consists in placing orthotic insoles in the shoes. Such insoles support the foot in the right position. Some are also used to protect the foot, ankle, knee and various other body structures from the impact associated with walking, running or athletic competition. Problems of the foot and lower leg are frequently corrected or at least compensated for or controlled by the utilization of an appropriate orthese.

There is principally two types of orthotic insoles, that is, active and passive.

The first type is mostly used as a comfort alternative in specific uses such as for obese persons or expectant mothers. They are also used for weight distribution and for their insulating qualities.

The passive type of insoles is used to overcome the lack of support and to recreate a normal condition for the ankle of the foot. Passive insoles may also be employed for distribution of weight.

The method, according to the present invention provides information relating to the condition of the foot and identifies the proper shoe and proper insole in order to reach the optimal biomechanical interaction in running, walking or standing.

In recent years, many technics have been developed in the field of orthotic insoles and ortheses to evaluate and compensate for certain malformations of the foot.

U.S. Pat. No. 4,062,355 (Kaye) shows a device for use in making biomechanical or orthopedic evaluation of the lower leg and foot employing a heel stationing arrangement to automatically provide a reference line parallel to the vertical bisection of the calcaneus bone. This evaluation is made by measuring the angular deformity of the forefoot and the rearfoot. Further, the device has an attachment to measure the dorsiflexion and plantar flexion of the foot about the ankle.

U.S. Pat. No. 3,358,373 (Martin) shows an angulation gauge having a gauge piece for engagement with the sole of the foot and with a height adjustable post rotationally mounted on the gauge piece having an index in association with the gauge piece. A knee-line sighting plate on the upper end of the post is sighted by a handle and is adjustable thereby to bring the index to the calibration on the gauge that visually shows the angle between the sighted line and the line from the ankle joint that is normal to the sole.

U.S. Pat. No. 2,175,116 (Hack et al.) presents a foot measuring device comprising means for determining the proper size and shape of a shoe to be fitted to the foot and has other means for simultaneously ascertaining several dimensions of the foot whereby a correlation of all dimensions may be obtained at a single examination.

The main drawback of the apparatuses of the prior art is that same are complex to use and most of all, they are best operated by professionals. Therefore, the technics are not available to the public on a day to day basis. The result of this, is that people have the tendency to neglect their feet conditions.

OBJECTS OF THE PRESENT INVENTION

It is a first object of the present invention to provide a simple, effective and non expensive method of evaluating the functional biomechanic type of the foot.

A second object of the present invention is to provide an objective method as above described which is easy to use by a non professional.

A third object of the present invention is to provide a method as above described which will provide the necessary compensation for the malformation of a person's foot.

Another object of the present invention is to provide a step by step method to evaluate the orthopedic need of a person such as an athlete.

A still other object of the invention is to provide a method to give information relating to a person's foot in order to select the proper shoe/insole to reach the optimal biomechanical interaction in different type of sports like running, tennis playing, walking, etc.

A further object of the present invention is to provide a measuring device used in connection with said above described method.

It is a still further object of the invention to provide a new and improved orthotic insole used in conjunction with the above described method.

These and other objects of the present invention will be obtained by a method for determining the functional biomechanic type of a person's foot comprising the following steps:

placing the person's foot in a neutral (unloaded) position;
identifying the center line of the heel bone;
identifying the center line of the tendo Achillis;
placing the person tested in a standing position preferably on a mirror table;
measuring the angle between the heel bone center line and the tendo Achillis center line when the person is standing with knees preferably bent at approximately 45° (135°).

The method may also comprise the following steps:
determining the type of arch of the foot;
measuring the lateral movement of the malleol bone, as the person tested moves from an approximative 45° bent knee position to a normal standing position;
and measuring of the forward flexibility of the ankle joint.

DESCRIPTION OF DRAWINGS

FIG. 1 shows an analysis sheet to be used with the method according to the present invention.

FIG. 5 shows an embodiment of a measuring device to evaluate the angular deformity of the forefoot which may be used with the method according to the present invention.

FIGS. 10, 11 and 12 show an embodiment of an insole for a left foot in accordance with the present invention.

FIGS. 10A, 10B and 10C are cross-sectional views taken generally along the lines 10A, 10B and 10C, respectively, in FIG. 10.

DESCRIPTION OF A PREFERRED EMBODIMENT

The foot testing method, according to the present invention, will now be described. The results of each step is written down on an analysis sheet. One embodiment of said analysis sheet is shown in FIG. 1. Column "A" represents the various steps of the method according to the present invention. Each of these steps will be hereinafter described. Columns "B" and "C" are to be filled in with the values obtained by the method respectively for the left foot and the right foot.

Each of columns "B" and "C" is preferably divided in a plurality of sections each corresponding to a particular type of pronation. In the embodiment shown in FIG. 1, columns "B" and "C" are each divided into three sections "O" for overpronation, "N" for near normal or normal pronation and "U" for under pronation. For each step, the results corresponding to the type of pronation is marked in the applicable section. Each section of each step may also be provided with a predetermined relative weight factor which is used in compiling the final results of the test. In FIG. 1, such factors are shown in the lower portion of the squares corresponding to the intersection of each step and each section. The factors are added up in each section. The section with the highest total determines the type of pronation. Each of sections "O", "N" and "U" is preferably color coded which a coding scheme corresponding to the one used with the measuring device 235 (see FIG. 4) and the various insoles (see FIGS. 6, 7 and 8).

When the sheet is completed, the adequate orthopedic insole is chosen by applying the test results to a predetermined table (not shown) which provides for a predetermined insole preferably in combination with a predetermined type of shoe to be used to correct any objectively identified deficiency.

The first step is to identify the center line of the heel bone and of the tendo Achillis. This is done by marking signal dots to the unloaded foot, which is held in a neutral position for example, the position shown in FIG. 2. This line will be used to later compare the deformations in the foot when its loaded.

Figure 2:
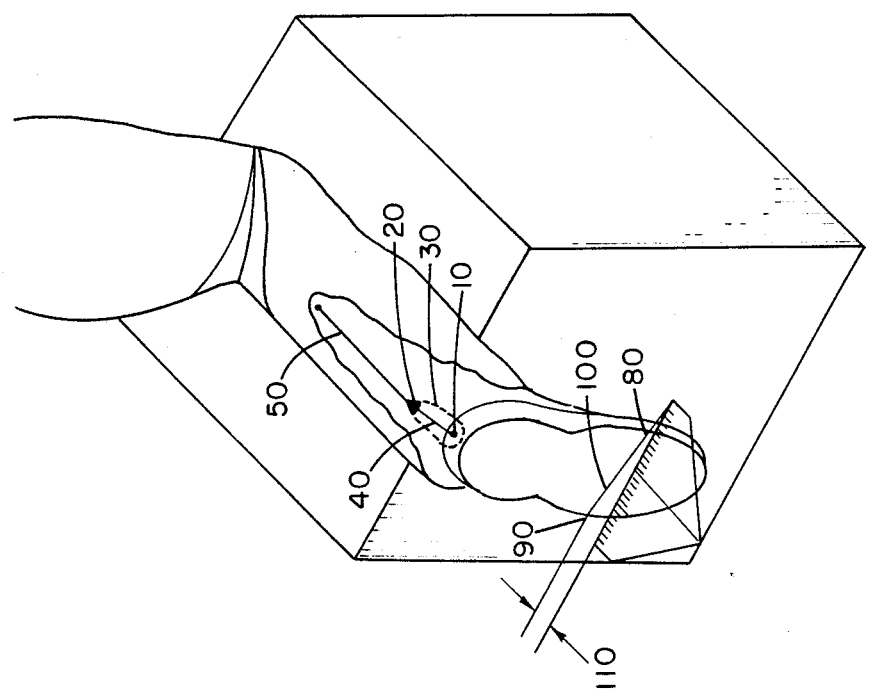
FIG. 2 shows a position of the foot which may be used for identifying the heel bone center line as well as the tendo Achillis center line in accordance with the invention (the shoe and any sock must be removed prior to tracing the center line).
Figure 4:
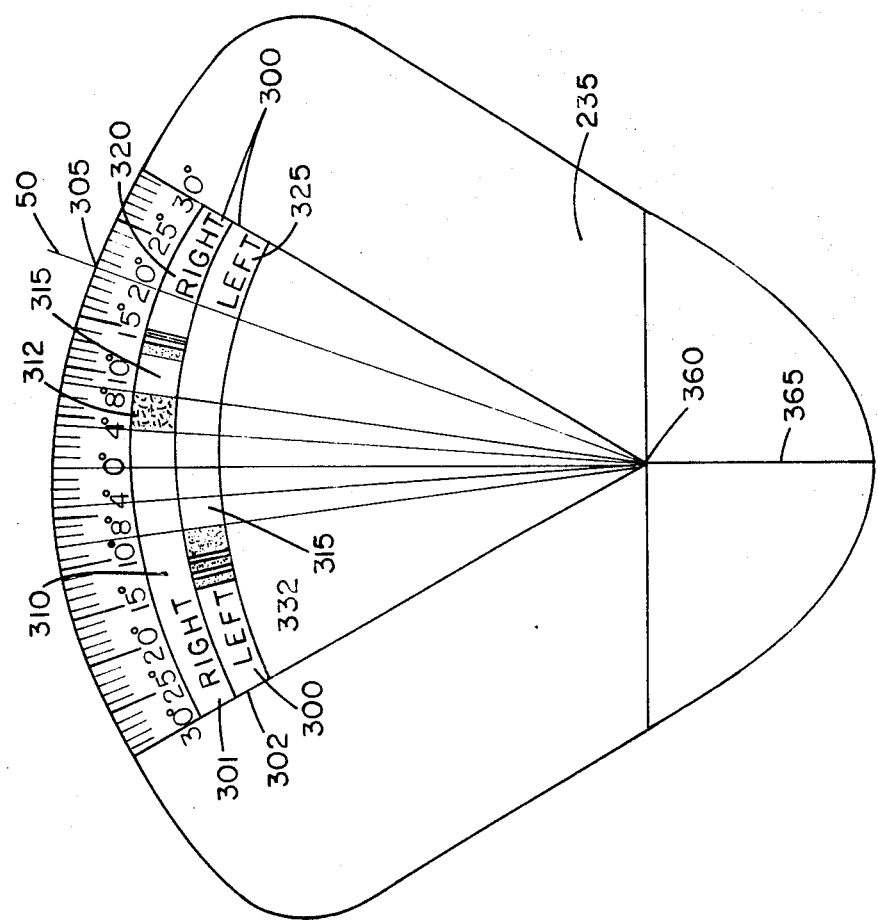
FIG. 4 shows an embodiment of an angle meter in accordance with the present invention to measure the functional biomechanic type of a right foot.
Figure 4:
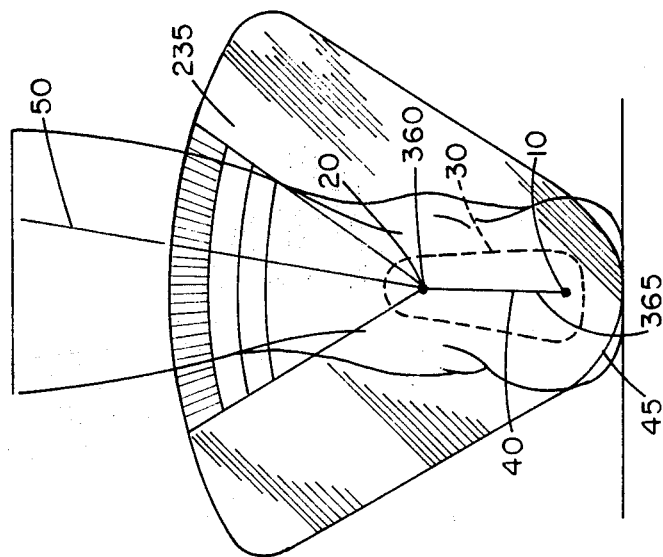

As shown in FIGS. 2 and 4, a first dot 10 is drawn on the lower part of the heel or calcaneous bone 30 (shown in dotted line) along the bisection line of same. Said bisection line is found by palpation or by feeling said bone. The second dot 20 is drawn on the intersection of the tendo Achillis with the upper portion of the heel bone 30.

Having now marked down the two dots 10 and 20, a first line 40 is then traced between said first and said second dots and a second line 50 is drawn over the tendo Achillis.

The second step is to evaluate the varus or valgus position of the forefoot at the level of the big toe 80 and little toe 90 joints using a straight line 100 as shown in FIG. 2. The first two steps are repeated for the second foot. Then, the deformation corresponds to the height 110 and the value is marked in column "B" or "C" according to the foot which is being evaluated.

Figure 3:
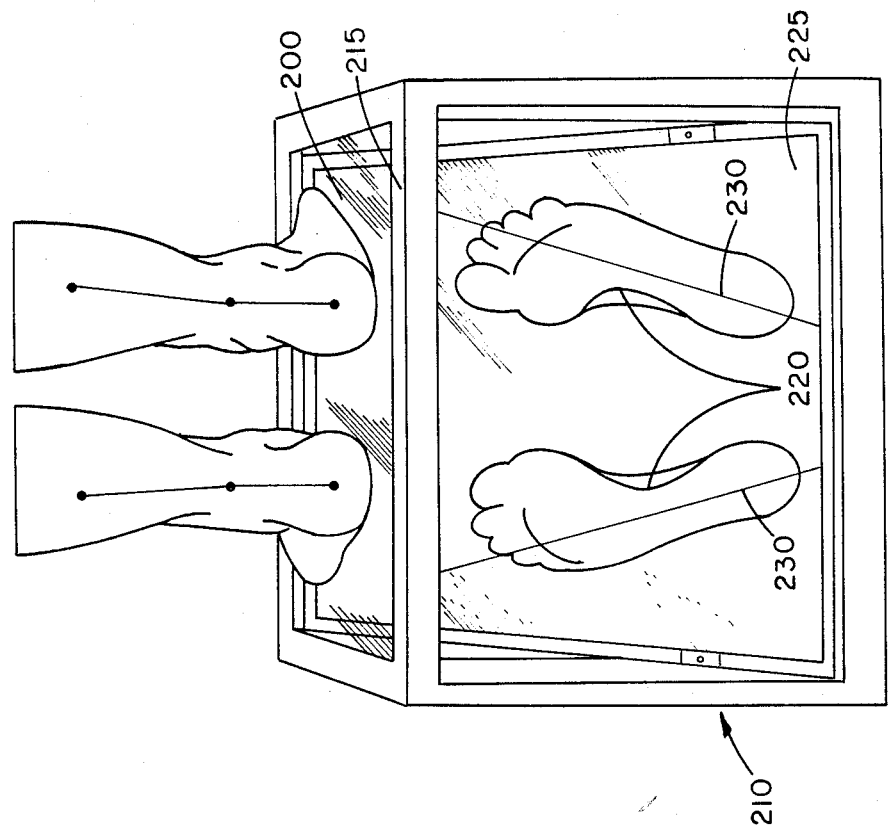
FIG. 3 shows a mirror table which may be used with the method according to the present invention.

For the rest of the evaluation, with reference to FIG. 3, the person preferably stands upon the glass panel 200 of a mirror table 210 (see FIG. 3) with his (her) feet placed at a certain distance from the edge 215 of said glass panels so that a clear reflected view of the bottom of the feet 220 is obtained on the inclined mirror 225 underneath the horizontal glass panel 200. It is important that the person should be asked to stand on the mirror table by placing his (her) feet along the premarked line 230 so as to obtain reliable and accurate information.

The third step is to determine the type of arch of each foot by comparing the reflected image 220 obtained on the mirror table 210 to the three types of feet A, B, C, shown in FIG. 1 as step number 3.

The fourth step is to determine by means of the measuring device 235 (shown in FIG. 4 and to be described later) the angle between the line 40 and the line 50 of each foot when the user's knees are bent at approximately 45°, so as to simulate running conditions. The result gives us the pronation angle and is reported on the analysis sheet of FIG. 1 as step number 4.

The fifth step illustrated on FIG. 1 as number 5 consists of measuring the lateral movement of the malleol bone 240 of each foot as the person tested moves from a 45° bent knee position to the normal standing position. This is accomplished by placing a measuring device 250 besides the ankle and measuring the distance between said measuring device 250 and ankle. The measuring device 250 is shown in detail in FIG. 5.

The angle 255 of the measuring device 250 should preferably be 135° to be usable to place the person tested in a perfect 45° bent knee position. To do so, the measuring device 250 is placed behind the knee joint of said person. It is to be understood that any similar measuring device may be used for this purpose.

The last step, that is the sixth, shown in FIG. 1 as number 6, is the measurement of the forward flexibility obtained by a measuring angle meter 260 placed beside the appropriate foot when the latter is dorsiflexed. The angle is then read off the scale and the result is reported on the analysis sheet.

Having now explained the method to evaluate the pronation angle and to report the result on the analysis sheet of FIG. 1, the measuring device 235 used in step 4 of the above described method will be hereinafter described.

Said measuring device shown in FIG. 4, comprises a visual coding system 300 having a first visually coded band 301, a second visually coded band 302, a graduation band 305, a reference point 360 and a reference line 365.

Said first band 301 is used to determine the pronation angle of the right foot whereas the second band 302 is used for the left foot.

As explained earlier, the analysis sheet, the measuring device as well as the corresponding insole are preferably visually coded (for example, for the right foot, a first color corresponding to under pronation 310, a second color corresponding to slightly over pronation 312 and a third color 320, to excessive over pronation) so as to facilitate the determination of the person's need. However, it should be understood that any similar visual coding may be used for the same purpose, such as letters, geometric forms or the like.

Figure 8:
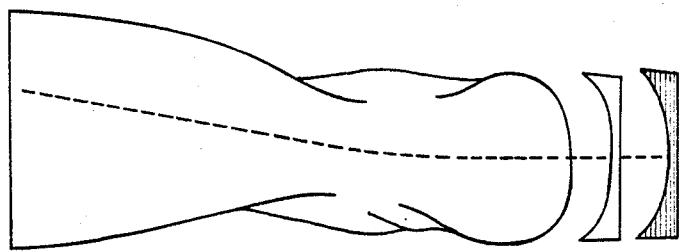
FIGS. 6, 7 and 8 show different types of pronation of the right foot.
Figure 7:
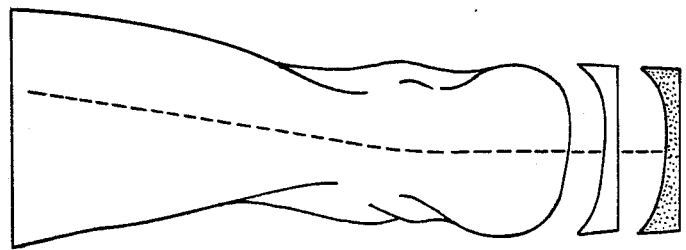
Figure 6:
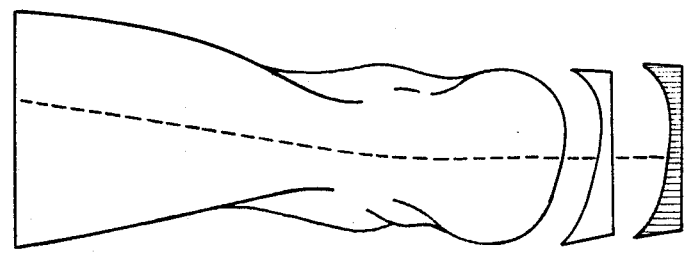

FIGS. 6 to 8 show these three common types of deformation of the right foot, that is respectively, excessive over pronation, slight over pronation and under pronation which correspond respectively to the coded bands 310, 312 and 320 of the measuring device for the right foot. For the left foot, under pronation is referred as number 325, slightly over pronation to number 332 and excessive over pronation to number 330, whereas the deformation of the foot corresponds to a mirror image of FIGS. 6 to 8.

In FIG. 4, there is shown a right foot 45 having an over pronation problem. When the angle meter 235 is used according to the fourth step of the present invention to measure the pronation angle it is placed behind the foot so as to place the reference point 360 on the second dot 20 traced on the heel bone by the first step and the reference line 365 is aligned with line 40. The pronation angle may then be read by reading off the scale in band 305. The pronation type may also be determined rapidly by looking at the color of band 301 (corresponding to the right foot in the present example) which extends over line 50.

In the example of FIG. 4, the color of the proper insole would have been red, that is to say, that the line 50 stands in the red coded band 320 of the measuring device 235. Such an insole is designed to correct excessive over pronation of the person's foot. In order to check the effect of the insole on the person's pronation, the person should be asked to step on the insole and the pronation angle measured one more time. If the excessive pronation has been properly corrected, the line 50 should stand in the clear (or normal) zone 315 of the angle meter. Another clear zone 315 is provided in the second band 302 for the left foot.

Figure 9:
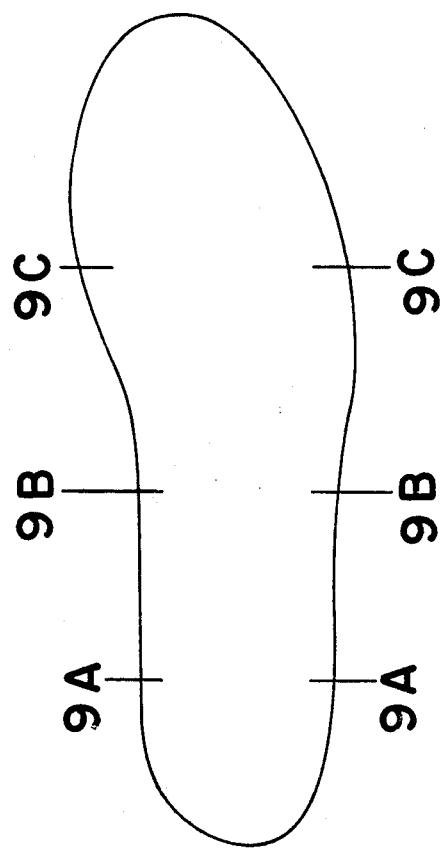
FIG. 9 shows a conventional prior art insole for a left foot.
Figure 9C:
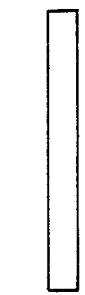
FIGS. 9A, 9B and 9C are cross-sectional views taken generally along the lines 9A, 9B and 9C, respectively, in FIG. 9.
Figure 9B:
Figure 9A:

FIGS. 10, 11 and 12 show an insole 399 used in conjunction with the above described method whereas FIG. 9 shows a conventional insole. Said insole 399 comprises a first portion 400 and a second portion 410. The first portion 400 being stiff whereas the second is made of flexible material such as polyurethane. Said first portion 400 comprises a higher portion 420 to shape the flexible material 410 and to lift the person's heel to correct the excessive pronation. The stiff portion 400 goes from the heel 430 to the ball 440 whereas the flexible portion 410 covers the entire length of the insole.

The advantage of using a stiff portion is to give a good support to the heel bone since flexible material tends to break down after use.

It is to be understood that various modifications, additions, changes and variations may be made to this method without departing from the spirit and scope of the invention.

We claim:

1. A method for determining the functional biomechanic type of a person's foot comprising the following steps:
   placing the person's foot in a neutral and unloaded position;
   identifying the center line of the heel bone;
   identifying the center line of the tendo Achillis;
   placing the person tested in a standing position;
   measuring the angle between the heel bone center line and the tendo Achillis center line when the person stands with the knees bent at approximately 45° (or 135° between the upper leg and the lower leg) determining the functional biomechanic type of the person's foot based on said angle measurement.

2. A method as described in claim 1, further comprising the step of placing the person tested in a standing position on a mirror table wherein said determining step further includes the step of determining the type of arch of the foot by comparing the reflected image obtained on the mirror table to a plurality of predetermined types of feet.

3. A method as described in claim 1, further comprising the step of placing the person tested in a standing position on a mirror table wherein said determining step further includes the step of determining the type of arch of the foot by comparing the reflecting image obtained on the mirror table to a plurality of predetermined types of feet and measuring the lateral movement of the malleol bone as the person tested moves from at approximately 45° bent knee position to a normal standing position.

4. A method as described in claim 1, further comprising the step of placing the person tested in a standing position on a mirror table wherein said determining step further includes the step of determining the type of arch of the foot by comparing the reflected image obtained on the mirror table to a plurality of predetermined types of feet and measuring the forward flexibility of the ankle joint.

5. A method as described in claim 1, further comprising the step of placing the person tested in a standing position on a mirror table wherein said determining step further includes the step of determining the type of arch of the foot by comparing the reflected image obtained on the mirror table to a plurality of predetermined types of feet and measuring the lateral movement of the malleol bone as the person tested moves from at approximately 45 ° bent knee position to a normal standing position and measuring the forward flexibility of the ankle joint.

6. A method as described in claim 1, wherein the tendo Achillis center line is identified by tracing a line on the person's skin.

7. A method as described in claim 6, further comprising the step of placing the person tested in a standing position on a mirror table wherein said determining step further includes the step of determining the type of arch of the foot by comparing the reflected image obtained on the mirror table to a plurality of predetermined types of feet.

8. A method as described in claim 6, further comprising the step of placing the person tested in a standing position on a mirror table wherein said determining step further includes the step of determining the type of arch of the foot by comparing the reflected image obtained on the mirror table to a plurality of predetermined types of feet and measuring the lateral movement of the malleol bone as the person tested moves from at approximately 45° bent knee position to a normal standing position.

9. A method as described in claim 2, further comprising the step of placing the person tested in a standing position on a mirror table wherein said determining step further includes the step of determining the type of arch of the foot by comparing the reflected image obtained on the mirror table to a plurality of predetermined types of feet and measuring the forward flexibility of the ankle joint.

10. A method as described in claim 6, further comprising the step of placing the person tested in a standing position on a mirror table wherein said determining step further includes the step of determining the type of arch of the foot by comparing the reflected image obtained on the mirror table to a plurality of predetermined types of feet and measuring the lateral movement of the malleol bone as the person tested moves from at approximately 45° bent knee position to a normal standing position and measuring the forward flexibility of the ankle joint.

11. A method as described in claim 2 wherein said heel center line is identified by placing a first dot and a second dot on the person's skin.

12. A method as described in claim 11, further comprising the step of placing the person tested in a standing position on a mirror table wherein said determining step further includes the step of determining the type of arch of the foot by comparing the reflected image obtained on the mirror table to a plurality of predetermined types of feet.

13. A method as described in claim 11, further comprising the step of placing the person tested in a standing position on a mirror table wherein said determining step further includes the step of determining the type of arch of the foot by comparing the reflected image obtained on the mirror table to a plurality of predetermined types of feet and measuring the lateral movement of the malleol bone as the person tested moves from at approximately 45° bent knee position to a normal standing position.

14. A method as described in claim 11, further comprising the step of placing the person tested in a standing position on a mirror table wherein said determining step further includes the step of determining the type of arch of the foot by comparing the reflecting image obtained on the mirror table to a plurality of predetermined types of feet and measuring the forward flexibility of the ankle joint.

15. A method as described in claim 11, further comprising the step of placing the person tested in a standing position on a mirror table wherein said determining step further includes the step of determining the type of arch of the foot by comparing the reflected image obtained on the mirror table to a plurality of predetermined types of feet and measuring the lateral movement of the malleol bone as the person tested moves from at approximately 45° bent knee position to a normal standing position and measuring the forward flexibility of the ankle joint.

16. A method for determining the functional biomechanic type of a person's foot and for pronation deficiencies, comprising the following steps:
   placing the person's foot in a neutral and unloaded position;
   identifying the center line of the heel bone;
   identifying the center line of the tendo Achillis;
   placing the person tested in a standing position on a mirror table and determining the type of arch of the foot by comparing the reflected image obtained on the mirror table to a plurality of predetermined type of feet and reporting the result on a test sheet comprising a subnormal pronation section, a normal pronation section and an above normal pronation section;
   measuring the angle between the heel bone center line and the tendo Achillis center line when the person stands with the knees bent at approximately 45° (or 135° between the upper leg and the lower leg) using an angle meter and reporting the result in a section of said test sheet corresponding to the measured angle determining the functional biomechanic type of the person's foot from the test sheet results.

17. A method as described in claim 16, wherein the test sheet is selected such that it comprises a plurality of visual codes each corresponding to a particular pronation type.

18. A method as described in claim 16, wherein the test sheet is selected such that it comprises a plurality of visual codes each corresponding to a pronation type and said angle meter comprises a plurality of visual codes identical to those of said test sheet.

19. A method as described in claim 16, further comprising the step of choosing an appropriate insole by correlating said test results to a predetermined selection table.

20. A method as described in claim 16, further comprising the step of choosing a appropriate insole by correlating said test results to a predetermined selection table and wherein the test sheet is selected such that it comprises a plurality of visual codes each corresponding to a particular pronation type and said insoles are visually coded using said test sheet visual codes.

21. A method as described in claim 16, further comprising the step of measuring the varus or the valgus position of the foot at the level of the big toe and little toe joint using a straight line and reporting the result in a corresponding section of the test sheet.

22. A method as described in claim 21, wherein the test sheet is selected such that it comprises a plurality of visual codes each corresponding to a particular pronation type.

23. A method as described in claim 21, wherein the test sheet is selected such that it comprises a plurality of visual codes each corresponding to a pronation type and said angle meter comprises a plurality of visual codes identical to those of said test sheet.

24. A method as described in claim 21, further comprising the step of choosing an appropriate insole by correlating said test results to a predetermined selection table.

25. A method as described in claim 21, further comprising the step of choosing an appropriate insole by correlating said test results to a predetermined selection table and wherein the test sheet is selected such that it comprises a plurality of visual codes each corresponding to a particular pronation type and said insoles are visually coded using said test sheet visual codes.

26. A method as described in claim 21, further comprising the step of measuring the lateral movement of the malleol bone as the person's tested moves from a 45° bent knee position to a normal standing position and reporting the result in a corresponding section of the test sheet.

27. A method as described in claim 26, further comprising the step of measuring the forward angular flexibility of the ankle joint and reporting the result in a corresponding section of the test sheet.

28. A method as described in claim 26, wherein the test sheet is selected such that it comprises a plurality of visual codes each corresponding to a particular pronation type.

29. A method as described in claim 26, wherein the test sheet is selected such that it comprises a plurality of visual codes each corresponding to a pronation type and said angle meter comprises a plurality of visual codes identical to those of said test sheet.

30. A method as described in claim 26, further comprising the step of choosing an appropriate insole by correlating said test results to a predetermined selection table.

31. A method as described in claim 26, further comprising the step of choosing an appropriate insole by correlating said test results to a predetermined selection table and wherein the test sheet is selected such that it comprises a plurality of visual codes each corresponding to a particular pronation type and said insoles are visually coded using said test sheet visual codes.

* * * * *